United States Patent [19]
Maykel

[11] Patent Number: 4,741,110
[45] Date of Patent: May 3, 1988

[54] MEASUREMENT OF PERIPHERAL STRENGTH

[76] Inventor: William A. Maykel, 36 Stark Rd., Worcester, Mass. 01602

[21] Appl. No.: 21,631

[22] Filed: Mar. 4, 1987

Related U.S. Application Data

[60] Continuation of Ser. No. 772,877, Sep. 5, 1985, abandoned, which is a division of Ser. No. 612,346, May 21, 1985, Pat. No. 4,539,756.

[51] Int. Cl.$^4$ .............................. A61F 3/00; G01B 3/20
[52] U.S. Cl. ............................................ 33/162; 33/515
[58] Field of Search ............... 33/515, 162, 168 R, 33/3 A, 536, 537, 534; 128/774, 779, 80 R, 614

[56] References Cited

U.S. PATENT DOCUMENTS

| | | |
|---|---|---|
| 1,348,861 | 8/1920 | Frye . |
| 1,951,322 | 3/1934 | Bliss . |
| 2,441,511 | 5/1948 | Ross .................................. 33/3 A |
| 2,846,772 | 8/1958 | Strausser ..................... 33/168 R X |
| 3,432,934 | 3/1969 | Schmidt . |
| 3,664,031 | 5/1970 | Duffy ............................. 33/162 X |

FOREIGN PATENT DOCUMENTS 849058  9/1952  Fed. Rep. of Germany ....... 33/3 A Primary Examiner—Harry N. Haroian
Attorney, Agent, or Firm—Blodgett & Blodgett

[57] ABSTRACT

System for measuring the limit of peripheral strength, consisting of method and apparatus for raising the heel of a patient in discreet steps while testing for peripheral strength.

3 Claims, 2 Drawing Sheets

MEASUREMENT OF PERIPHERAL STRENGTH

This is a continuation of co-pending application Ser. No. 772,877 filed on Sept. 5, 1985, which is a division of application Ser. No. 612,346 filed May 21, 1985, now U.S. Pat. No. 4,539,756.

BACKGROUND OF THE INVENTION

In medical practice, and particularly in connection with chiropractic procedures, it is important to know in an individual patient the amount of calcaneal (heel) elevation at which peripheral strength drops off. The knowledge of the particular degree of heel lift at which peripheral strength is substantially reduced is important, not only as a diagnostic tool, but also in connection with an active treatment of the patient. It is also important to the patient that he should know how his body is affected by excessive heel elevation. This relatively overlooked factor has tremendous impact on functional body stability. Attempts in the past to measure this particular element in bodily function have been expensive and difficult to operate. These and other difficulties experienced with the prior art devices have been obviated in a novel manner by the present invention.

It is, therefore, an outstanding object of the invention to provide a gage to measure the point of heel elevation at which peripheral strength is lost.

Another object of this invention is the provision of a method of measuring the point in heel elevation in which the strength of arm motion and other peripheral elements is substantially reduced.

A further object of the present invention is the provision of a peripheral strength gage which is capable of providing a simple means to increase heel elevation in discreet steps.

It is another object of the instant invention to provide a peripheral strength gage which is simple in construction, which is inexpensive to manufacture, and which is capable of a long life of useful service with a minimum of maintenance.

Another object of the invention is the provision of a peripheral strength gage in which heel elevation can be increased acurately in steps and which is very simple to use without danger to the patient.

With these and other objects in view, as will be apparent to those skilled in the art, the invention resides in the combination of parts set forth in the specification and covered by the claims appended hereto.

SUMMARY OF THE INVENTION

In general, the invention consists of a gage to measure the point of heel elevation at which peripheral strength is lost, comprising a support structure adapted to rest on a flat horizontal first surface. A plate is connected to the support structure and has a second surface, which is inclined at a selected angle to the first surface. In this way, a patient can be tested by placing him in a standing position with the heels of both feet on the second surface. The foot angle between the first surface (on the one hand) and the plane of the balls and heels (on the other hand) being changed in successive steps while measuring peripheral strength at each step to observe the step at which peripheral strength begins to decrease. Markings are provided, including horizontal lines, to indicate the heel elevation or foot angle at the successive steps.

More specifically, the method may consist of using the second surface at a fixed angle to the first surface and this being provided with markings to indicate the foot angle as the heels are moved upwardly on the second surface from one marking to another, or the second surface may be adjustable to different angles relative to the first surface, the balls and heels remaining in fixed positions on the surface, while the angle of the second surface is adjusted.

BRIEF DESCRIPTION OF THE DRAWINGS

The character of the invention, however, may be best understood by reference to one of its structural forms, as illustrated by the accompanying drawings, in which.

DESCRIPTION OF THE PREFERRED EMBODIMENT

Figure 1:
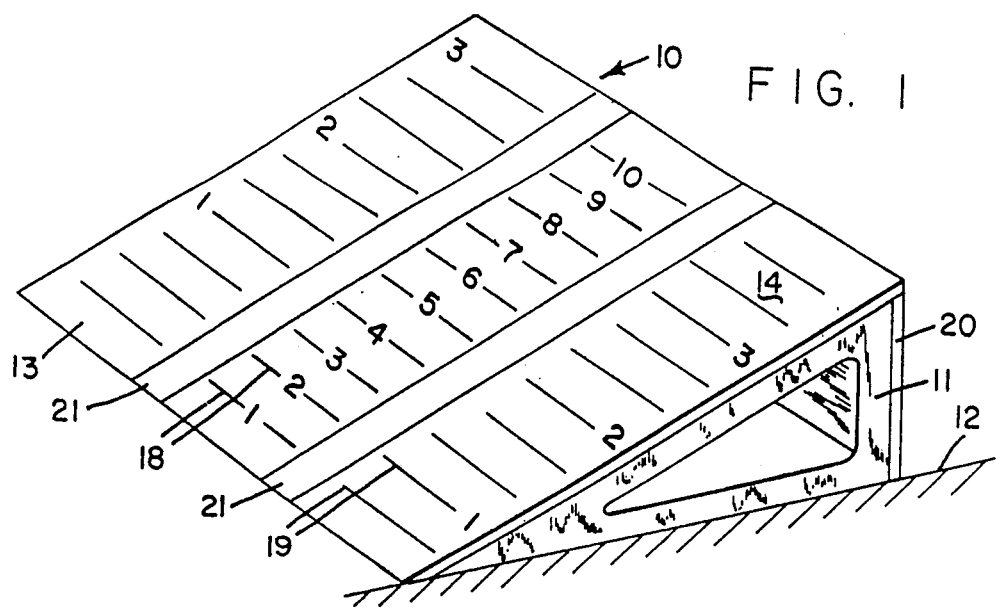
FIG. 1 is a perspective view of a gage incorporating the principles of the present invention.

Referring first to FIG. 1, which best shows the general features of the invention, the gage 10, indicated generally by the reference numeral 10, is formed to measure the point of heel elevation at which peripheral strength is lost. It consists of a support structure 11 that is adapted to rest on a flat horizontal first surface 12. A plate 13 is connected to the support structure 11 and is provided with a second surface 14. This second surface is inclined at a selected angle to the first surface, so that a patient to be tested can be placed in a standing position with the balls 16 of both feet 15 on the said first surface and with the heels 17 of both feet 15 on the second surface. The foot angle between the first surface (on the one hand) and the plane of the balls 16 and heels 17 (on the other hand) is changed in successive steps, while measuring peripheral strength at each step to observe the step at which peripheral strength begins to decrease. Markings 18, including horizontal lines 19, are provided on the surface 14.

A brace 20 extends between the support structure 11 and the plate 13 to hold them at the fixed angle. The markings 18 are provided on the second surface to indicate the foot or elevation as the heels 17 are moved upwardly on the second surface from one marking to another.

A pair of spaced parallel stripes 21 are formed on the second surface to assist in locating the feet and the surface is provided with an abrasive coating to prevent slippage. The stripes extend at right angles to the horizontal lines 19 or, in other words, directly down the slope of the surface 14.

Figure 4:
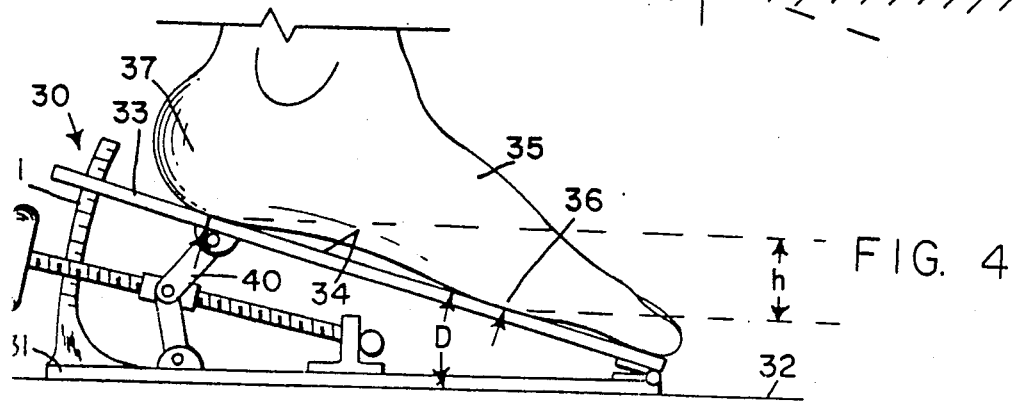
FIG. 4 shows a modified form of the gage.

Referring to FIG. 4, it can be seen that a modified form of the gage 30 is provided with a support structure 31 resting on the floor or first surface 32. The plate 33 is hingedly attached to the support structure 31 and is provided with a second surface 34. The patient's foot 35 is shown as resting on the surface 34 with the ball 36 in a low position and the heel 37 at a higher position. A protractor 41 extends from the support structure 31 upwardly past the surface 34 and is provided with markings 38. An adjustable brace 40, in the form of a toggle which is screw-operated, extends between the support structure 31 and the plate 33 to change the angle between them, thus changing, of course, the elevation of the heels 37 above the balls 36 of the foot 35. The feet with their balls and heels remain in fixed position on the second surface 34, while the angle of the second surface is adjusted, the angle or elevation of the heel being indicated by the protractor 41. Suitable stripes (not shown) extend down the surface 34.

Figure 2:
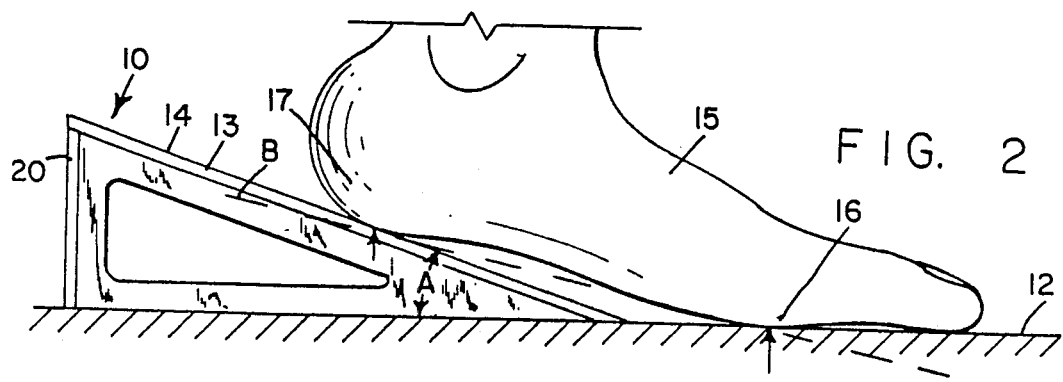
FIGS. 2 and 3 show the gage in use in different positions of the patient's foot.
Figure 3:
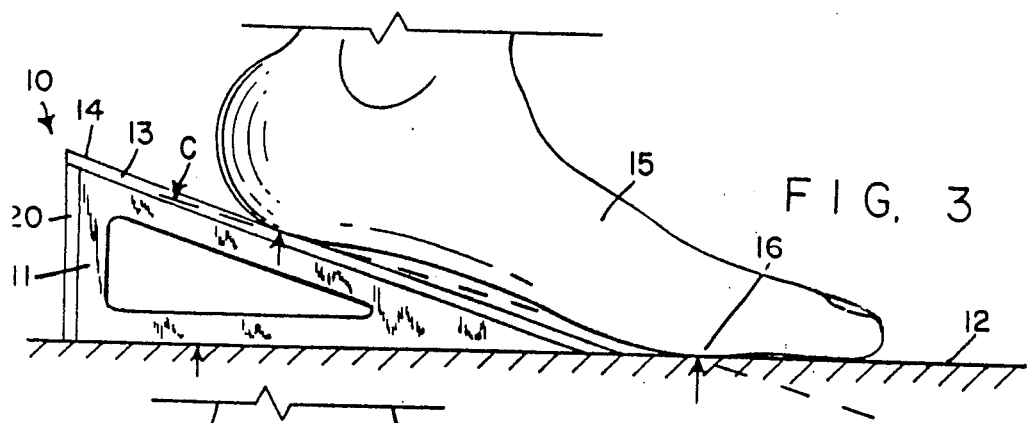
Figure 5:
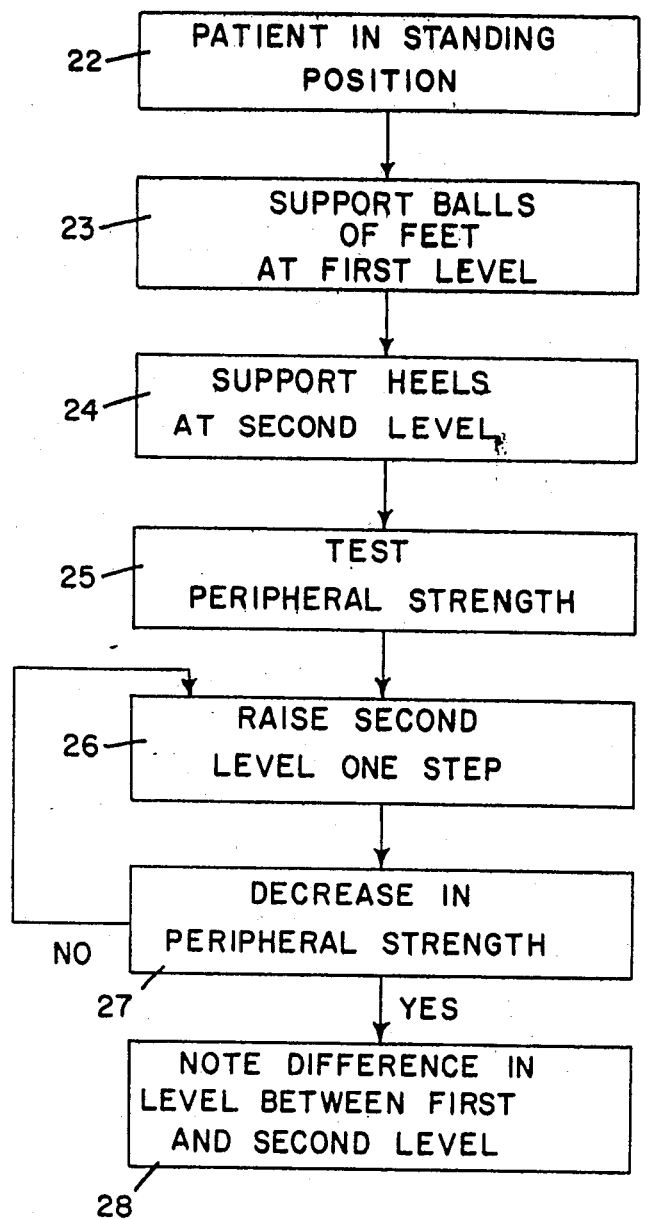
FIG. 5 is a flow chart showing the steps of the present method.

The operation and advantages of the invention will now be readily understood in view of the above description. Referring to FIG. 5, it can be seen that the procedure is carried out in a number of steps. In Step 22, the patient is placed in a standing position and in Step 23, the balls of both feet are placed on a common horizontal first level. Then, in Step 24, both heels are supported on a common second level. In Step 25, the peripheral strength is tested. This is a common procedure usually consisting of having the patient raise his arms while a degree of downward pressure is applied on the hands to see how much resistance to such pressure he is able to provide. Even to an inexperienced person, this strength is a matter of value judgement that is simple for him to perform. In Step 26, the heels are raised one discreet step and in Step 27 the peripheral strength is tested to see if there is a substantial decrease. If there is no decrease, then Step 26 is repeated by raising the heel one more step and the peripheral strength tested again for a decrease. By changing in successive steps, the distance between the first level (on the one hand) and the second level (on the other hand), while measuring the peripheral strength of the patient at each step, it is possible to carry out this procedure. Eventually, there will be a substantial decrease in peripheral strength. At that time, in accordance with Step 28, the difference will be noted in the level between the first and the second surfaces. This level can be expressed either in terms of inches (or centimeters) distance between the level of the balls of the feet and the heels of the feet, while the patient is standing perfectly vertically; or it can be expressed in terms of the angle. Referring to FIGS. 2 and 3, it can be seen that the present method for measuring the point of heel elevation at which peripheral strength is lost is shown as consisting in placing the patient to be tested in a standing position in accordance with Step 22, supporting the balls 16 of the feet 15 on the flat horizontal surface or on the floor surface 12. Both heels in accordance with Step 24 are supported on the surface 14 of the gage 10 which surfaces incline at a selected angle to the first surface 12. When the patient is in the position shown in FIG. 2, the peripheral strength is measured in accordance with Step 25. After that, by changing in successive steps, the elevation between the first surface and the second surface, eventually the condition is reached (shown in FIG. 3) in which the foot is located, so that the heel 17 is substantially above the heel 16 and the testing of peripheral strength in accordance with Step 27 shows a remarked decrease. The point at which this takes place is noted in accordance with Step 28 as being either so many inches above the position of the ball of the foot or so many centimeters, or in some cases by angularity. This knowledge is very helpful as a preventative screening procedure, as well as a diagnostic tool used on an active treatment basis. Referring to FIG. 4, when the apparatus shown there is used, the second surface 34 is adjustable to different angles relative to the first surface 32 and the balls and heels remain in fixed positions on the second surface.

Since calcaneal elevation imposes at a certain specific height, a marked inability of the human nervous system to function properly, the measurement by the present method and apparatus is very useful. Since simple muscle testing procedures clearly demonstrate the inability of the body to maintain peripheral muscle strength after a certain fixed point of heel elevation, this knowledge can be helpful to any patient and to the person who is treating this patient. The measurement is an important consideration for optimal health, especially where a patient's orthopedic welfare is concerned. It is clear that the device may be usefully used in a preventative screening procedure as well as a diagnostic tool to be used on an active treatment basis. Every person should know the functions of his own body and how it is affected by excessive heel elevation and this relatively overlooked fact has a tremendous impact on functional body stability. It can be seen, therefore, that the present invention can be of a very useful purpose in helping to lead a healthy life and in treating orthopedic disorders as well as other functional disorders secondary to instability in the musculo-skeletal system.

It is obvious that minor changes may be made in the form and construction of the invention without departing from the material spirit thereof. It is not, however, desired to confine the invention to the exact form herein shown and described, but it is desired to include all such as properly come within the scope claimed.

The invention having been thus described, what is claimed as new and desired to secure by Letters Patent is:

1. Gage to measure the point of heel elevation at which peripheral strength is lost, comprising:
    (a) a support structure adapted to rest on a flat first surface,
    (b) a plate connected to the support structure and having a second surface, which surface is inclined at a selected angle to the first surface and arranged to provide a clear path from said second surface to said first surface, so that a patient to be tested can be placed in a standing position with the balls of both feet on the said first surface and with the heels of both feet on the second surface, the foot angle between the first surface (on the one hand) and the plane of the balls and heels (on the other hand) being changed in successive steps while measuring peripheral strength at each step to observe the step at which peripheral strength begins to decrease,
    (c) means applied to said inclined second surface and essentially in the same plane as said second surface to support and hold the patient's heel against downward sliding movement,
    (d) markings including horizontal lines to indicate the heel position at the successive steps, the said means of supporting the patient's heel comprising a pair of spaced, parallel strips of abrasive material extending perpendicular to said horizontal lines, and
    (e) an adjustable brace extending between the support structure and the plate to change the angle between them, the balls and heels remaining in fixed positions on the two surfaces, while the angle of the second surface is adjusted, the markings being located on a protractor extending between the support structure and the plate.

2. Gage to measure the point of heel elevation at which peripheral strength is lost, comprising:
    (a) a support structure adapted to rest on a flat first surface,
    (b) a plate connected to the support structure and having a second surface, which surface is inclined at a selected angle to the first surface and arranged to provide a clear path from said second surface to said first surface, so that a patient to be tested can be placed in a standing position with the balls of both feet on the said first surface and with the heels of both feet on the second surface, the foot angle between the first surface (on the one hand) and the plane of the balls and heels (on the other hand) being changed in successive steps while measuring peripheral strength at each step to observe the step at which peripheral strength begins to decrease, (c) means applied to said inclined second surface and essentially in the same plane as said second surface to support and hold the patient's heel against downward sliding movement, (d) markings on the said second surface of the plate, the markings including horizontal lines to indicate the heel position at the successive steps, the said means of supporting the patient's heel comprising a pair of spaced, parallel strips of abrasive material extending perpendicular to said horizontal lines, and (e) a brace extending between the support structure and the plate to hold them at a fixed angle, and wherein the markings are provided on the second surface to indicate the heel elevation as the heels are moved upwardly on the second surface from one marking to another.

3. Gage to measure the point of heel elevation at which peripheral strength is lost, comprising:

(a) a support structure adapted to rest on a flat first surface, (b) a plate connected to the support structure and having a second surface, which surface is inclined at a selected angle to the first surface and arranged to provide a clear path from said second surface to said first surface, so that a patient to be tested can be placed in a standing position with the balls of both feet on the said first surface and with the heels of both feet on the second surface, the foot angle between the first surface (on the one hand) and the plane of the balls and heels (on the other hand) being changed in successive steps while measuring peripheral strength at each step to observe the step at which peripheral strength begins to decrease, (c) means applied to said inclined second surface and essentially in the same plane as said second surface to support and hold the patient's heel against downard sliding movement, (d) markings including horizontal lines to indicate the heel position at the successive steps, the said means of supporting the patient's heel comprising a pair of spaced, parallel strips of abrasive material extending perpendicular to said horizontal lines.

* * * * *